(12) United States Patent
Ma et al.

(10) Patent No.: US 11,427,870 B2
(45) Date of Patent: Aug. 30, 2022

(54) METHOD FOR TREATING ENCAPSULATING PERITONEAL SCLEROSIS

(71) Applicant: National Central University, Taoyuan (TW)

(72) Inventors: Nian-Han Ma, Taoyuan (TW); Chiu-Chin Huang, Taichung (TW); Jin-Bor Chen, Taoyuan (TW); Chin-Chung Tseng, Tainan (TW); I-Kuan Wang, Taichung (TW); Chien-Lung Chen, Taoyuan (TW); An-Lun Li, Taoyuan (TW)

(73) Assignee: National Central University, Taoyuan (TW)

( * ) Notice: Subject to any disclaimer, the term of this patent is extended or adjusted under 35 U.S.C. 154(b) by 0 days.

(21) Appl. No.: 16/924,793

(22) Filed: Jul. 9, 2020

(65) Prior Publication Data
US 2021/0388440 A1 Dec. 16, 2021

(30) Foreign Application Priority Data
Jun. 11, 2020 (TW) .................... 109119580

(51) Int. Cl.
*C12Q 1/6883* (2018.01)

(52) U.S. Cl.
CPC ....... *C12Q 1/6883* (2013.01); *C12Q 2537/16* (2013.01); *C12Q 2600/112* (2013.01); *C12Q 2600/178* (2013.01)

(58) Field of Classification Search
None
See application file for complete search history.

(56) References Cited

U.S. PATENT DOCUMENTS

2011/0015080 A1* 1/2011 Golub .................. C12Q 1/6834
506/2

FOREIGN PATENT DOCUMENTS

| CN | 104144178 A | 11/2014 |
|----|-------------|---------|
| TW | 200538120 A | 12/2005 |
| TW | 201250005 A | 12/2012 |
| TW | 201315473 A | 4/2013 |
| TW | 201348450 A | 12/2013 |
| TW | 201439122 A | 10/2014 |
| TW | 201514308 A | 4/2015 |
| TW | 201608028 A | 3/2016 |
| TW | 201625797 A | 7/2016 |
| TW | 201723479 A | 7/2017 |
| TW | 201802716 A | 1/2018 |

OTHER PUBLICATIONS

Chen et al Disease Markers. 2012. 33: 35-42 (Year: 2012).*
Tumilson et al. Molecular Neurobiology. 2014. 50: 545-558 (Year: 2014).*
Tian et al. PLOS One. Jan. 5, 2012. 7(1): e29551 (Year: 2012).*
Zhou et al. Scientific Reports. Jun. 10, 2015. 6:11251 (Year: 2016).*
Heggardetal International Journal of Cancer. May 4, 2011. 102. 130: 1378-1386 (Year: 2011).*
Min et al BMC Genomics. 2010. 11:96 (Year: 2010).*
Huang et al. Kidney Week. Nov. 2019. "Identifying miRNA Biomarkers for Diagnosis of Encapsulating Peritoneal Sclerosis," Abstract FR-OR103 (Year: 2019).*
Huang et al J Am Soc Nephrology. 2019. 60: 69; abstract for conference "Kidney Week 2019" held Nov. 5, 2019 to Nov. 10, 2019, first available Dec. 31, 2020 (Year: 2020).*
Bhatt, Kirti , et al., "Anti-Inflammatory Role of MicroRNA-146a in the Pathogenesis of Diabetic Nephropathy", J Am Soc Nephrol 27: 2277-2288, 2016. doi: 10.1681/ASN.2015010111.
Che, Mingwen , et al., "The MicroRNA-199a/214 Cluster Targets E-Cadherin and Claudin-2 and Promotes High Glucose-Induced Peritoneal Fibrosis", J Am Soc Nephrol 28: 2459-2471, 2017. doi:https://doi.org/10.1681/ASN.2016060663.
Danford, Christopher , et al., "Encapsulating peritoneal sclerosis", World J Gastroenterol Jul. 28, 2018; 24(28):3101-3111.
Habib, S.M. , et al., "Management of encapsulating peritoneal sclerosis: a guideline on optimal and uniform treatment", The Netherlands Journal of Medicine. Nov./Dec. 2011, vol. 69, No. 11.
Li, Dong , et al., "Human umbilical cord mesenchymal stem cells facilitate the up-regulation of miR-153-3p, whereby attenuating MGO-induced peritoneal fibrosis in rats", J Cell Mol Med. 2018;22. https://doi.org/10.1111/jcmm.13622, Mar. 3, 2018, 3452-3463.
Lin, Fan , et al., "A microrna screen to identify regulators of peritoneal fibrosis in a rat model of peritoneal dialysis", BMC Nephrology (2015) 16:48 DOI 10.1186/s12882-015-0039-z.
Ma, Ya-Li , et al., "MicroRNA-21 promotes the progression of peritoneal fibrosis through the activation of the TGF-β/Smad signaling pathway: An in vitro and in vivo study", International Journal of Molecular Medicine 41:1030-1038, 2018, 1030-1038.
Morishita, Yoshiyuki , et al., "MicroRNA expression profiling in peritoneal fibrosis", Translational Research. vol. 169, Mar. 2016, pp. 47-66, https://doi.org/10.1016/j.trsl.2015.10.009.
Tseng, Chin-Chung , et al., "Incidence and outcomes of encapsulating peritoneal sclerosis (EPS) and factors associated with severe EPS", PLoS ONE 13(1): e0190079. https://doi.org/10.1371/journal.pone.0190079, Jan. 2, 2018, 1-13.

(Continued)

Primary Examiner — Carla J Myers

(57) ABSTRACT

A method for estimating a risk for a subject suffering from encapsulating peritoneal sclerosis is provided, including measuring an expression level of at least one microRNA from a sample of the subject, and the microRNA is selected from miR-17, miR-100, miR-155, miR-202, miR-422a, and miR-483; comparing the expression level of the microRNA in the sample to that of a same miRNA of a control, when the expression level of miRNA in the sample is lower than that of the control, the subject is estimated having the risk of encapsulating peritoneal sclerosis. A kit for estimating a risk for a subject suffering from encapsulating peritoneal sclerosis is also provided, including at least one agent for identifying the at least one microRNA as above mentioned from the sample of the subject.

8 Claims, 7 Drawing Sheets

Specification includes a Sequence Listing.

(56) References Cited

OTHER PUBLICATIONS

Xiao, Li, et al., "MicroRNA-129-5p modulates epithelial-to-mesenchymal transition by targeting SIP1 and SOX4 during peritoneal dialysis", Laboratory Investigation (2015) 95, 817-832; doi:10.1038/labinvest.2015.57; published online May 11, 2015.

Yu, Jian-Wen, et al., "MicroRNA-29b inhibits peritoneal fibrosis in a mouse model of peritoneal dialysis", Laboratory Investigation (2014) 94, 978-990; doi:10.1038/labinvest.2014.91; published online Jul. 21, 2014.

Zhang, Yiming, et al., "Apigenin suppresses mouse peritoneal fibrosis by down-regulating miR34a expression", Biomedicine & Pharmacotherapy 106 (2018) 373-380, Jun. 25, 2018.

Applied Biosystems, "TaqMan® MicroRNA Assays Protocol", 2006. https://genome.med.harvard.edu/documents/qpcr/microRNATaqManAssayProtocol.pdf (ref. 14).

Brook, Amy, "Local microRNAs in Peritoneal Dialysis-Related Peritonitis", Cardiff University, 2019. (ref. 13).

\* cited by examiner

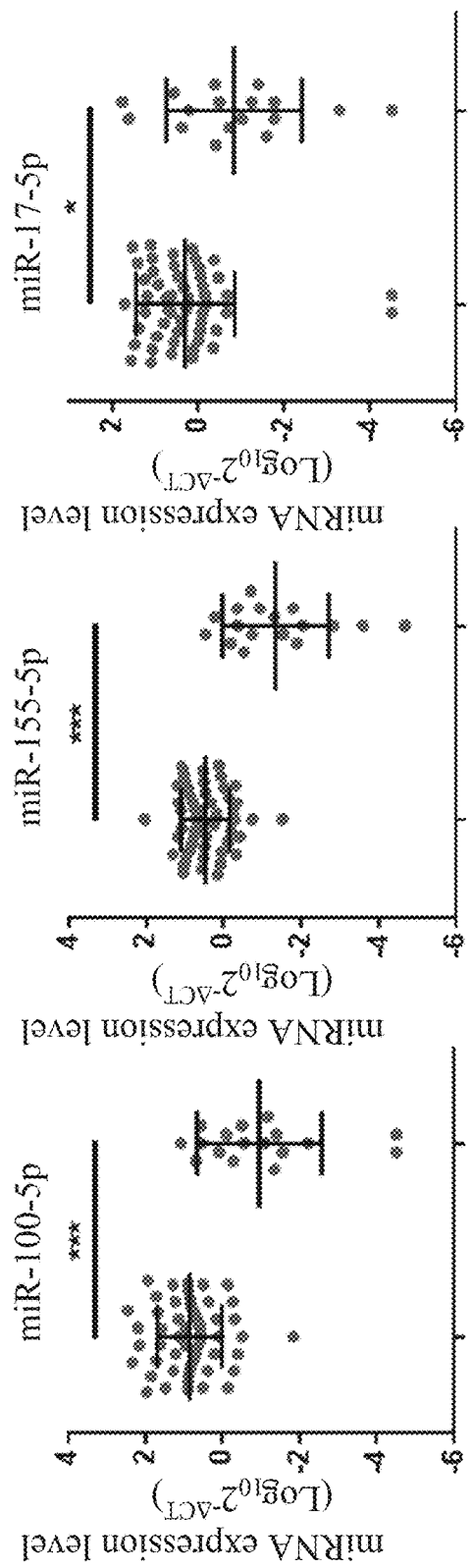
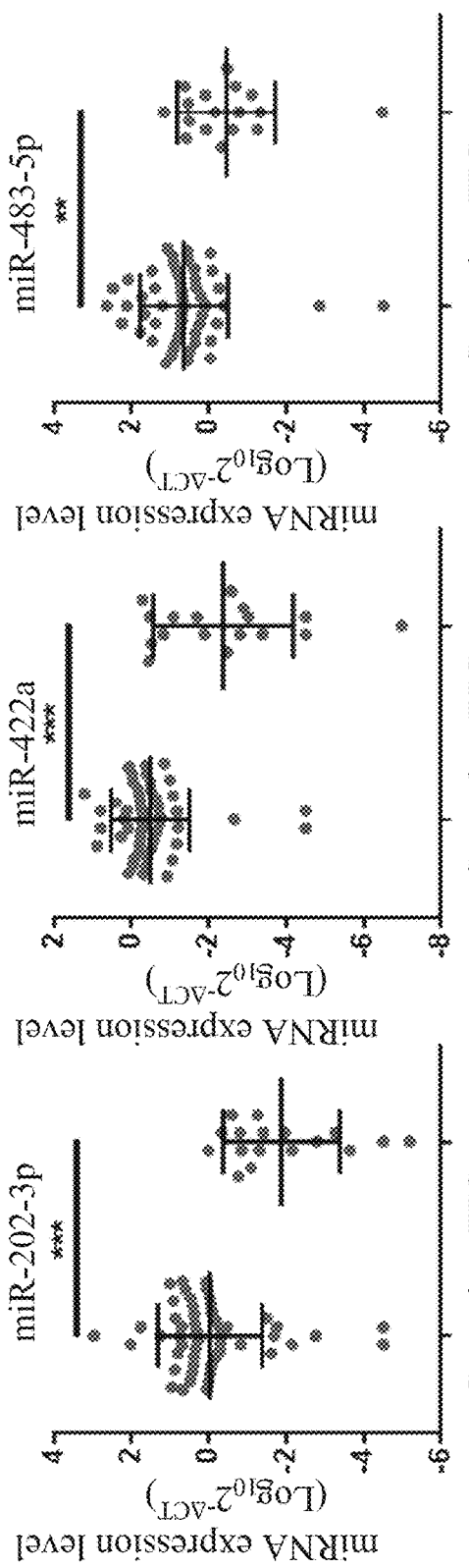

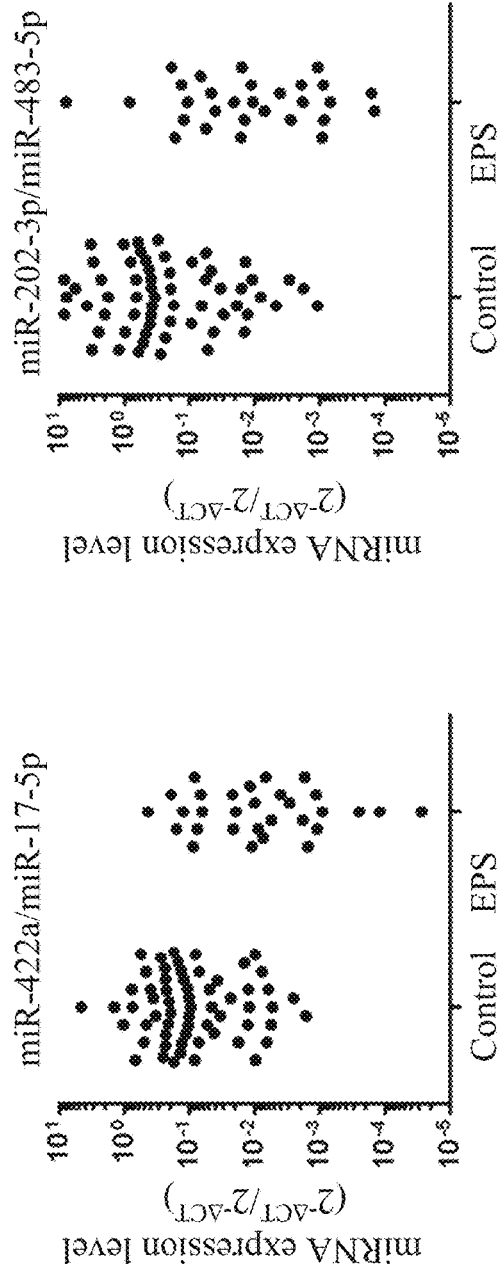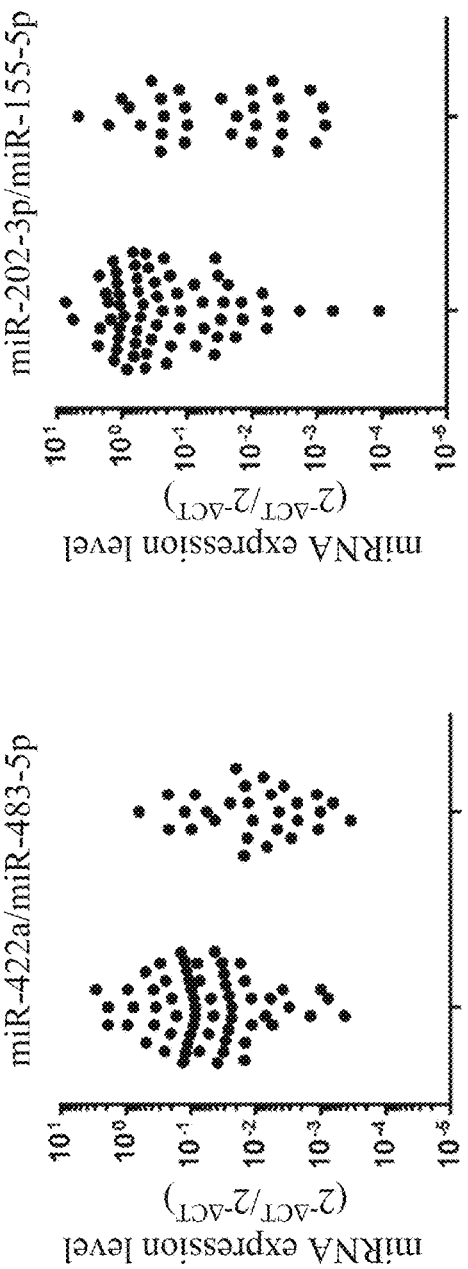

METHOD FOR TREATING ENCAPSULATING PERITONEAL SCLEROSIS

CROSS-REFERENCE TO RELATED APPLICATION

This application claims priority to Taiwan Application Serial Number 109119580, filed on Jun. 11, 2020, which is herein incorporated by reference in its entirety.

The Sequence Listing associated with this application is filed in electronic format via EFS-Web and is hereby incorporated by reference into the specification in its entirety. The name of the text file containing the Sequence Listing is 2002012_ST25.txt. The size of the text file is 1.46 KB, and the text file was created on Jul. 9, 2020.

BACKGROUND

Field of Invention

The present invention relates to an estimating method, analyzer and kit thereof. More particularly, the present invention relates to a method for estimating a risk for a subject suffering from encapsulating peritoneal sclerosis, analyzer and kit thereof.

Description of Related Art

Encapsulating peritoneal sclerosis (EPS) is a rare and serious complication of long-term peritoneal dialysis (PD), and the mortality of the long-term peritoneal dialysis may be positively related to the severity of encapsulating peritoneal sclerosis. Current clinical symptoms of the encapsulating peritoneal sclerosis include abdominal pain, poor appetite, nausea, vomiting, and weight loss. The encapsulating peritoneal sclerosis is diagnosed by the radiological features and invasive laparoscopy. Although current studies have attempted to monitor the occurrence of encapsulating peritoneal sclerosis by plasma proteins, there are still no practical biomarkers available clinically.

Therefore, developing biomarkers for detecting encapsulating peritoneal sclerosis is needed, and the disadvantage of the prior art should be resolved.

SUMMARY

The present disclosure provides a method and a kit for estimating a risk for a subject suffering from an encapsulating peritoneal sclerosis, and a highly accurate detection effect is achieved in a non-invasive way.

The present disclosure provides the method for estimating a risk for a subject suffering from an encapsulating peritoneal sclerosis, the method comprising steps of: measuring an expression level of at least one micro ribosomal nucleic acid (miRNA) in a sample of the subject, wherein the miRNA is selected from the group consisting of miR-17, miR-100, miR-155, miR-202, miR-422a, and miR-483; and comparing the expression level of the miRNA in the sample to that of a same miRNA of a control, wherein when the expression level of miRNA in the sample is lower than that of the control, the subject is estimated having a risk of suffering from the encapsulating peritoneal sclerosis.

In one embodiment, the control is obtained from a group of subjects without the encapsulating peritoneal sclerosis.

In one embodiment, the subject is a patient receiving peritoneal dialysis.

In one embodiment, the sample comprises ascites, blood, urine, feces, gastric juice, or bile.

The present disclosure also provides a method for estimating a risk for a subject suffering from an encapsulating peritoneal sclerosis, the method comprising steps of: measuring expression levels of two miRNAs in a sample of the subject, wherein the two miRNAs are selected from the group consisting of miR-17, miR-100, miR-155, miR-202, miR-422a, and miR-483; calculating a first ratio, the first ratio obtained from dividing one of the expression levels of the two miRNAs by the other one of the expression levels of the two miRNAs of the sample of the subject; providing a reference value; and comparing the first ratio and the reference value to obtain a comparing result, wherein the comparing result is used for estimating the risk for a subject suffering from the encapsulating peritoneal sclerosis.

In one embodiment, the first ratio in the step of calculating is obtained from calculating the expression levels of the two miRNAs in the sample of the subject by formulae (1) to (10):

$$\frac{\text{expression level of miR-422a}}{\text{expression level of miR-17}} = \text{a first ratio A}; \quad \text{formula (1)}$$

$$\frac{\text{expression level of miR-202}}{\text{expression level of miR-483}} = \text{a first ratio B}; \quad \text{formula (2)}$$

$$\frac{\text{expression level of miR-422a}}{\text{expression level of miR-483}} = \text{a first ratio C}; \quad \text{formula (3)}$$

$$\frac{\text{expression level of miR-202}}{\text{expression level of miR-155}} = \text{a first ratio D}; \quad \text{formula (4)}$$

$$\frac{\text{expression level of miR-202}}{\text{expression level of miR-17}} = \text{a first ratio E}; \quad \text{formula (5)}$$

$$\frac{\text{expression level of miR-100}}{\text{expression level of miR-17}} = \text{a first ratio F}; \quad \text{formula (6)}$$

$$\frac{\text{expression level of miR-155}}{\text{expression level of miR-17}} = \text{a first ratio G}; \quad \text{formula (7)}$$

$$\frac{\text{expression level of miR-100}}{\text{expression level of miR-483}} = \text{a first ratio H}; \quad \text{formula (8)}$$

$$\frac{\text{expression level of miR-202}}{\text{expression level of miR-422a}} = \text{a first ratio I}; \quad \text{formula (9)}$$

or $$\frac{\text{expression level of miR-155}}{\text{expression level of miR-483}} = \text{a first ratio J}; \quad \text{formula (10)}$$

In one embodiment, the step of providing the reference value comprises: calculating the reference value, the reference value divided one of the expression levels of the two miRNAs in a sample of a control by the other one of the expression levels of the two miRNAs of the control to obtain a second ratio, wherein the two miRNAs of the control are the same as that of the subject, wherein the second ratio is obtained from calculating the expression levels of the two miRNAs in the sample of the control by formulae (1-1) to (10-1):

$$\frac{\text{expression level of miR-422a}}{\text{expression level of miR-17}} = \text{a second ratio A}; \quad \text{formula (1-1)}$$

$$\frac{\text{expression level of miR-202}}{\text{expression level of miR-483}} = \text{a second ratio B;} \quad \text{formula (2-1)}$$

$$\frac{\text{expression level of miR-422a}}{\text{expression level of miR-483}} = \text{a second ratio C;} \quad \text{formula (3-1)}$$

$$\frac{\text{expression level of miR-202}}{\text{expression level of miR-155}} = \text{a second ratio D;} \quad \text{formula (4-1)}$$

$$\frac{\text{expression level of miR-202}}{\text{expression level of miR-17}} = \text{a second ratio E;} \quad \text{formula (5-1)}$$

$$\frac{\text{expression level of miR-100}}{\text{expression level of miR-17}} = \text{a second ratio F;} \quad \text{formula (6-1)}$$

$$\frac{\text{expression level of miR-155}}{\text{expression level of miR-17}} = \text{a second ratio G;} \quad \text{formula (7-1)}$$

$$\frac{\text{expression level of miR-100}}{\text{expression level of miR-483}} = \text{a second ratio H;} \quad \text{formula (8-1)}$$

$$\frac{\text{expression level of miR-202}}{\text{expression level of miR-422a}} = \text{a second ratio I;} \quad \text{formula (9-1)}$$

or $$\frac{\text{expression level of miR-155}}{\text{expression level of miR-483}} = \text{a second ratio J;} \quad \text{formula (10-1)}$$

wherein the step of comparing the first ratio and the reference value comprises when the comparing result is that the first ratio is less than the second ratio, the subject is estimated having the risk of suffering from the encapsulating peritoneal sclerosis.

In one embodiment, the control is obtained from a group of subjects without the encapsulating peritoneal sclerosis.

In one embodiment, the step of comparing the first ratio and the reference value comprises when the comparing result is that: when the first ratio A is less than or equal to a reference A0, when the first ratio B is less than or equal to a reference B0, when the first ratio C is less than or equal to a reference C0, when the first ratio D is less than or equal to a reference D0, when the first ratio E is less than or equal to a reference E0, when the first ratio F is less than or equal to a reference F0, when the first ratio G is less than or equal to a reference G0, when the first ratio H is less than or equal to a reference H0, when the first ratio I is less than or equal to a reference I0, or when the first ratio J is less than or equal to a reference J0, the subject is estimated having the risk of suffering from the encapsulating peritoneal sclerosis.

In one embodiment, the reference A0 is 0.2127, the reference B0 is 0.2017, the reference C0 is 0.1938, the reference D0 is 5.281, the reference E0 is 0.09099, the reference F0 is 2.718, the reference G0 is 0.28, the reference H0 is 2.448, the reference I0 is 1.045, or the reference J0 is 0.08035.

The present disclosure also provides a method for estimating a risk for a subject suffering from an encapsulating peritoneal sclerosis, the method comprising steps of: measuring expression levels of a plurality of miRNAs in a sample of the subject, wherein the plurality of the miRNAs comprise miR-17, miR-155, miR-202, miR-422a, and miR-483; calculating a plurality of first ratios, the first ratios obtained from calculating the expression levels of the plurality of the miRNAs in the sample of the subject by the following formulae:

$$\frac{\text{expression level of miR-422a}}{\text{expression level of miR-17}} = \text{a first ratio A;} \quad \text{formula (1)}$$

$$\frac{\text{expression level of miR-202}}{\text{expression level of miR-483}} = \text{a first ratio B;} \quad \text{formula (2)}$$

$$\frac{\text{expression level of miR-422a}}{\text{expression level of miR-483}} = \text{a first ratio C;} \quad \text{formula (3)}$$

$$\frac{\text{expression level of miR-202}}{\text{expression level of miR-155}} = \text{a first ratio D;} \quad \text{formula (4)}$$

and $$\frac{\text{expression level of miR-202}}{\text{expression level of miR-17}} = \text{a first ratio E;} \quad \text{formula (5)}$$

calculating the first ratios A, B, C, D, and E to obtain a prediction score S; providing a reference value S0; and estimating the risk for the subject suffering from the encapsulating peritoneal sclerosis, wherein when the prediction score S is less than or equal to the reference value S0, the subject is estimated having the risk of suffering from the encapsulating peritoneal sclerosis.

In one embodiment, the prediction score S is obtained from calculating the expression levels of the plurality of the miRNAs with an equation below:

$$\text{prediction score } S = -4.088 + (1.957*V) + (2.271*W) + (1.109*X) + (1.904*Y) - (0.108*Z) \quad \text{equation (11),}$$

wherein when the first ratio A is less than or equal to 0.2127, V=1, when the first ratio A is more than 0.2127, V=0; when the first ratio B is less than or equal to 0.2017, W=1, when the first ratio B is more than 0.2017, W=0; when the first ratio C is less than or equal to 0.1938, X=1, when the first ratio C is more than 0.1938, X=0; when the first ratio D is less than or equal to 5.281, Y=1, when the first ratio D is more than 5.281, Y=0; and when the first ratio E is less than or equal to 0.09099, Z=1, when the first ratio E is more than 0.09099, Z=0.

In one embodiment, the step of providing the reference value S0 comprises: measuring expression levels of a plurality of miRNAs in samples of a group of subjects with and without the encapsulating peritoneal sclerosis, wherein the plurality of the miRNAs comprise miR-17, miR-155, miR-202, miR-422a, and miR-483; and calculating a plurality of second ratios, the second ratios obtained from calculating the expression levels of the plurality of the miRNAs in the samples of the group of the subjects without the encapsulating peritoneal sclerosis by the following formulae:

$$\frac{\text{expression level of miR-422a}}{\text{expression level of miR-17}} = \text{a second ratio A;} \quad \text{formula (1-1)}$$

$$\frac{\text{expression level of miR-202}}{\text{expression level of miR-483}} = \text{a second ratio B;} \quad \text{formula (2-1)}$$

$$\frac{\text{expression level of miR-422a}}{\text{expression level of miR-483}} = \text{a second ratio C;} \quad \text{formula (3-1)}$$

$$\frac{\text{expression level of miR-202}}{\text{expression level of miR-155}} = \text{a second ratio D;} \quad \text{formula (4-1)}$$

and

-continued $$\frac{\text{expression level of miR-202}}{\text{expression level of miR-17}} = \text{a second ratio E;} \quad \text{formula (5-1)}$$

calculating a plurality of third ratios, the third ratios obtained from calculating the expression levels of the plurality of the miRNAs in the samples of the group of the subjects with the encapsulating peritoneal sclerosis by the following formulae:

$$\frac{\text{expression level of miR-422a}}{\text{expression level of miR-17}} = \text{a third ratio A;} \quad \text{formula (1-2)}$$

$$\frac{\text{expression level of miR-202}}{\text{expression level of miR-483}} = \text{a third ratio B;} \quad \text{formula (2-2)}$$

$$\frac{\text{expression level of miR-422a}}{\text{expression level of miR-483}} = \text{a third ratio C;} \quad \text{formula (3-2)}$$

$$\frac{\text{expression level of miR-202}}{\text{expression level of miR-155}} = \text{a third ratio D;} \quad \text{formula (4-2)}$$

and $$\frac{\text{expression level of miR-202}}{\text{expression level of miR-17}} = \text{a third ratio E;} \quad \text{formula (5-2)}$$

and calculating the second ratios A, B, C, D, and E and the third ratios A, B, C, D, and E by a receiver operating characteristic curve to obtain a cutoff value as the reference value S0.

The present disclosure also provides a kit for estimating a risk for a subject suffering from an encapsulating peritoneal sclerosis, the kit comprising: at least one reagent, the reagent using for detecting an expression level of at least one miRNA in a sample of the subject, wherein the miRNA is selected from the group consisting of miR-17, miR-100, miR-155, miR-202, miR-422a, and miR-483.

In one embodiment, the kit comprises a plurality of reagents using for detecting expression levels of the miR-155 and miR-17 in the sample of the subject, wherein the kit comprises a plurality of reagents using for detecting expression levels of the miR-155 and miR-483 in the sample of the subject, wherein the kit comprises a plurality of reagents using for detecting expression levels of the miR-202 and miR-483 in the sample of the subject, wherein the kit comprises a plurality of reagents using for detecting expression levels of the miR-155 and miR-422a in the sample of the subject, wherein the kit comprises a plurality of reagents using for detecting expression levels of the miR-422a and miR-17 in the sample of the subject, wherein the kit comprises a plurality of reagents using for detecting expression levels of the miR-422a and miR-483 in the sample of the subject, wherein the kit comprises a plurality of reagents using for detecting expression levels of the miR-202 and miR-17 in the sample of the subject, wherein the kit comprises a plurality of reagents using for detecting expression levels of the miR-100 and miR-483 in the sample of the subject, wherein the kit comprises a plurality of reagents using for detecting expression levels of the miR-155 and miR-100 in the sample of the subject, or wherein the kit comprises a plurality of reagents using for detecting expression levels of the miR-100 and miR-17 in the sample of the subject.

In one embodiment, the reagent comprises a pair of primers, probes, or a combination thereof.

The present disclosure also provides an analyzer for estimating a risk for a subject suffering from an encapsulating peritoneal sclerosis, the analyzer comprises a detection device, an arithmetic device, and a judgment device. The detection device detecting an expression level of at least one miRNA in a sample of the subject, wherein the miRNA is selected from the group consisting of miR-17, miR-100, miR-155, miR-202, miR-422a, and miR-483. The arithmetic device performing arithmetic operations on the expression levels of the miRNA, comprising comparing the expression level of the miRNA in the sample to that of a same miRNA of a control to obtain a comparing result. The judgment device determines the comparing result, wherein when the expression level of miRNA in the sample is higher than that of the control, the subject is estimated having a risk of suffering from the encapsulating peritoneal sclerosis. And the judgment device further advises the subject with a suitable therapy based on the comparing result.

In one embodiment, the control is obtained from a group of subjects without the encapsulating peritoneal sclerosis.

BRIEF DESCRIPTION OF THE DRAWINGS

The invention can be more fully understood by reading the following detailed description of the embodiment, with reference made to the accompanying drawings as follows.

FIG. 2 shows expression levels of miRNA-100-5p in the sample of control group and encapsulating peritoneal sclerosis (EPS) group according to one embodiment of the present disclosure.

FIG. 3 shows expression levels of miRNA-155-5p in the sample of control group and EPS group according to one embodiment of the present disclosure.

FIG. 4 shows expression levels of miRNA-17-5p in the sample of control group and EPS group according to one embodiment of the present disclosure.

FIG. 5 shows expression levels of miRNA-202-3p in the sample of control group and EPS group according to one embodiment of the present disclosure.

FIG. 6 shows expression levels of miRNA-422a in the sample of control group and EPS group according to one embodiment of the present disclosure.

FIG. 7 shows expression levels of miRNA-483-5p in the sample of control group and EPS group according to one embodiment of the present disclosure.

FIG. 8 shows expression levels of a ratio of miR-422a to miR-17-5p (miR-422a/miR-17-5p) in the sample of control group and EPS group according to one embodiment of the present disclosure.

FIG. 9 shows expression levels of miR-202-3p/miR-483-5p in the sample of control group and EPS group according to one embodiment of the present disclosure.

FIG. 10 shows expression levels of miR-422a/miR-483-5p in the sample of control group and EPS group according to one embodiment of the present disclosure.

FIG. 11 shows expression levels of miR-202-3p/miR-155-5p in the sample of control group and EPS group according to one embodiment of the present disclosure.

DETAILED DESCRIPTION

The following disclosure provides detailed description of many different embodiments, or examples, for implementing different features of the provided subject matter. These are, of course, merely examples and are not intended to limit the invention but to illustrate it. In addition, various embodiments disclosed below may combine or substitute one embodiment with another, and may have additional embodiments in addition to those described below in a beneficial way without further description or explanation.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

Although a series of operations or steps are used below to describe the method disclosed herein, an order of these operations or steps should not be construed as a limitation to the present invention. For example, some operations or steps may be performed in a different order and/or other steps may be performed at the same time. In addition, all shown operations, steps and/or features are not required to be executed to implement an embodiment of the present invention. In addition, each operation or step described herein may include a plurality of sub-steps or actions.

The present disclosure provides a method for estimating a risk for a subject suffering from encapsulating peritoneal sclerosis. In one embodiment, suitable situations for estimating the risk of encapsulating peritoneal sclerosis in the subject by the method of the present disclosure may include encapsulating peritoneal sclerosis induced by long-term peritoneal dialysis.

The subject may include, but not limited to, human, orangutan, monkey, cat, dog, rabbit, guinea pig, rat or mouse. In one embodiment, the subject may be a patient with dialysis.

Figure 1:
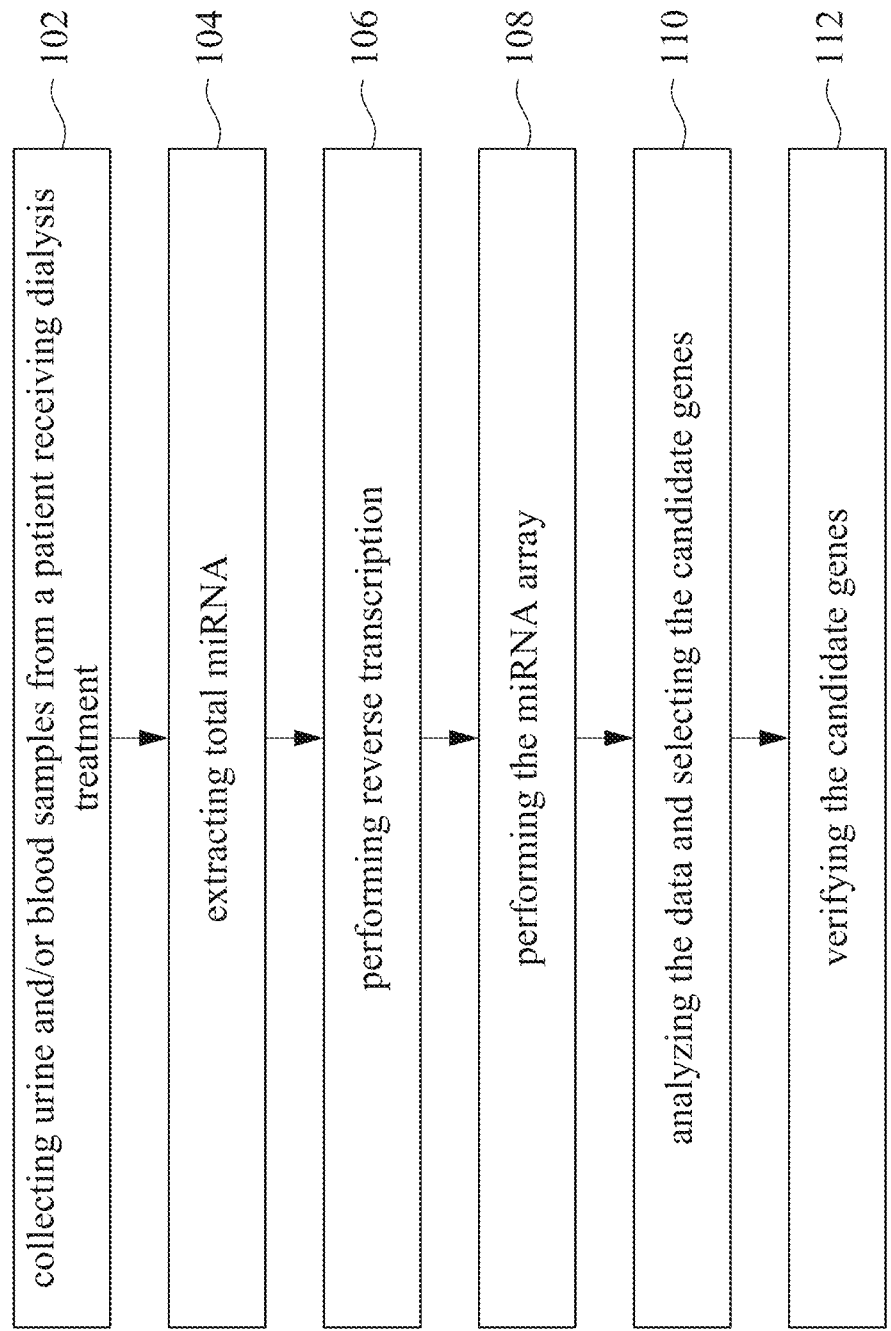
FIG. 1 shows a flow chart illustrating a screening process for detecting miRNAs in an encapsulating peritoneal sclerosis according to one embodiment of the present disclosure.
Figure 12:
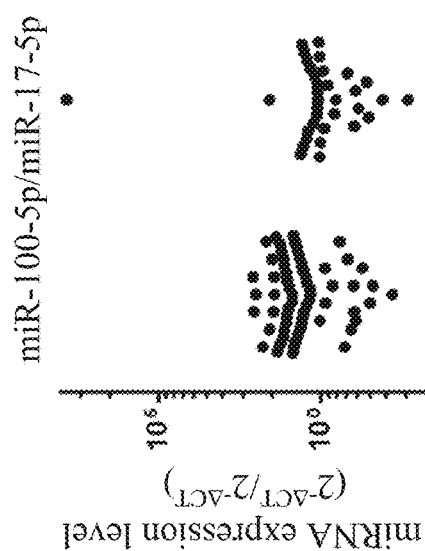
FIG. 12 shows expression levels of miR-202-3p/miR-17-5p in the sample of control group and EPS group according to one embodiment of the present disclosure.
Figure 13:
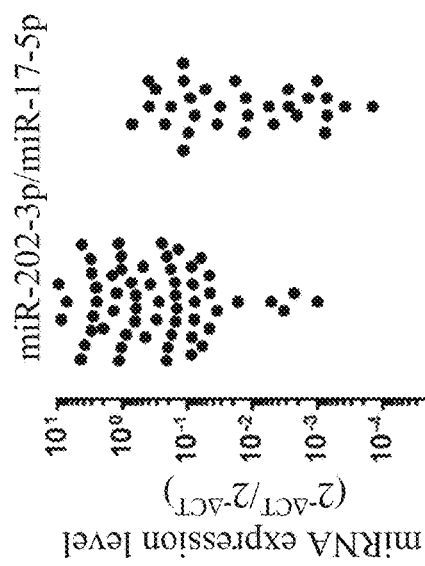
FIG. 13 shows expression levels of miR-100-5p/miR-17-5p in the sample of control group and EPS group according to one embodiment of the present disclosure.
Figure 14:
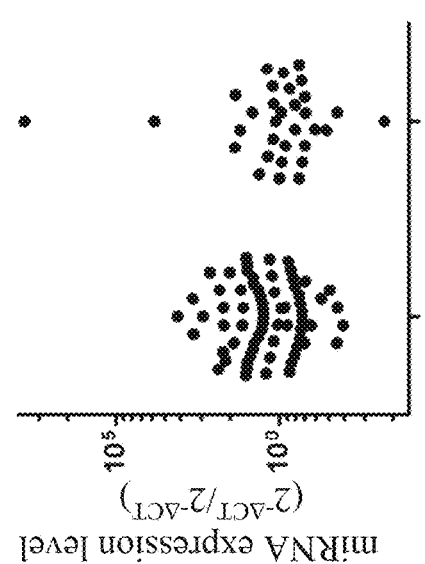
FIG. 14 shows expression levels of miR-155-5p/miR-17-5p in the sample of control group and EPS group according to one embodiment of the present disclosure.
Figure 15:
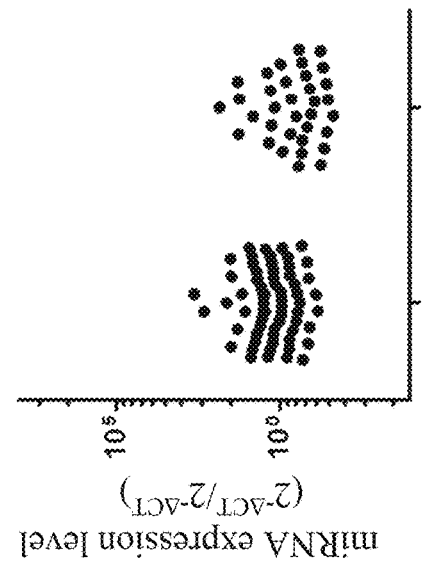
FIG. 15 shows expression levels of miR-100-5p/miR-483-5p in the sample of control group and EPS group according to one embodiment of the present disclosure.
Figures 16, 17:
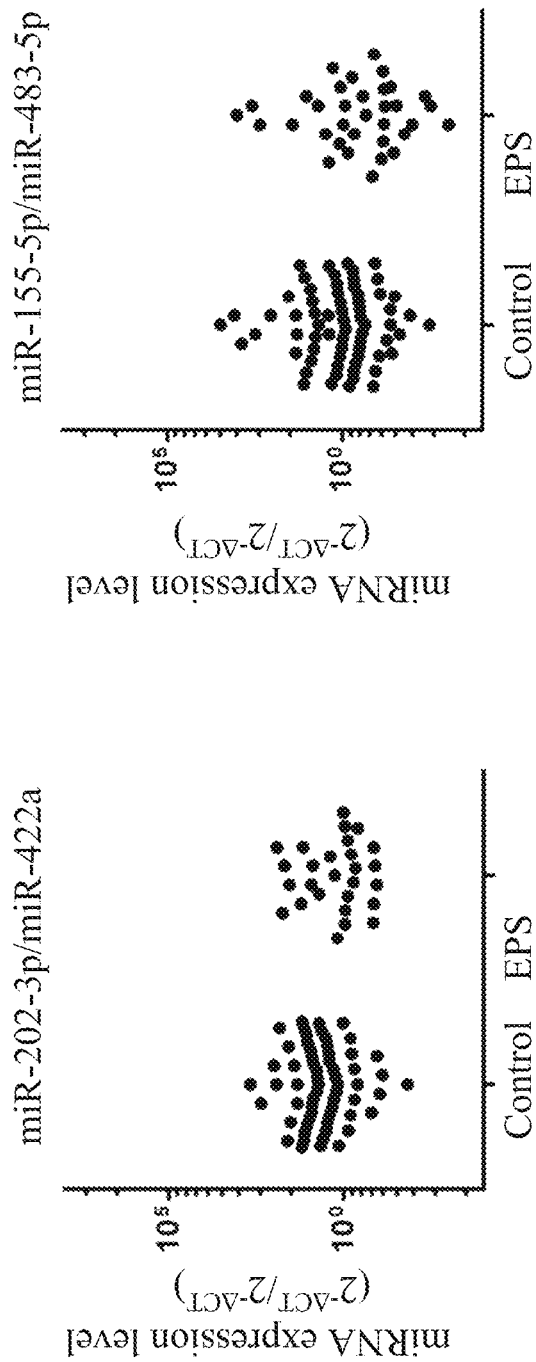
FIG. 16 shows expression levels of miR-202-3p/miR-422a in the sample of control group and EPS group according to one embodiment of the present disclosure.
FIG. 17 shows expression levels of miR-155-5p/miR-483-5p in the sample of control group and EPS group according to one embodiment of the present disclosure.

FIG. 1 is a flow chart for screening miRNAs associated with encapsulating peritoneal sclerosis.

The method 100 begins at step 102 collecting ascites samples from a patient receiving dialysis treatment. Because this group of patients had a high incidence of encapsulating peritoneal sclerosis, the differences of the expression levels of miRNAs between the patients without encapsulating peritoneal sclerosis (control group) and the patients with encapsulating peritoneal sclerosis (EPS group) were compared.

In some embodiments, the control group obtained a sample from a subject who did not ever have the encapsulating peritoneal sclerosis, a subject before dialysis, or a subject before accepting other therapy.

Then, step 104 is to extract total miRNA from the ascites sample. MiRNA is stable in human tissues and cell samples, and miRNA is not easily degraded. MiRNA can be detected in many body fluids such as blood, saliva, urine, and ascites. MiRNA in the patient's ascites samples was detected in some examples of the present disclosure.

In some embodiments, the "micro ribosomal nucleic acid (abbreviated microRNA or miRNA)" refers to a small non-coding RNA molecule containing about 19 to 25 nucleotides. MiRNA can recognize messenger RNA (mRNA) because of sequences specificity, so that the expression of the gene is regulated by inhibiting the transcription of the mRNA or degrading the mRNA.

After that, step 106 is to reverse transcribe the total miRNA into complementary DNA (cDNA).

Next, step 108 is to perform the miRNA array. The reverse transcription cDNA was detected by the miRNA array chip, and the chip detected the expression of miRNAs. For example, the chip of TaqMan® Array Human MicroRNA A Cards v2.0 can be used in detecting nearly 380 kinds of human miRNAs expression, and the cycle thresholds (CT) of the cDNAs of the target miRNAs can be obtained.

Further, step 110 is to analyze the data and select the candidate genes. According to the result of the miRNA array, certain miRNAs having significant different expression levels of the between patients with and without encapsulating peritoneal sclerosis can be selected. For example, some certain miRNAs were highly expressed in samples of patients with encapsulating peritoneal sclerosis, and some certain miRNAs were less expressed in samples of patients with encapsulating peritoneal sclerosis. These certain miRNAs can be used as candidate genes for the detection of encapsulating peritoneal sclerosis.

Furthermore, step 112 is to verify the candidate genes. For example, the expression levels of the candidate genes between the patients with and without encapsulating peritoneal sclerosis were measured by real-time polymerase chain reaction (real-time PCR).

In some embodiments, the method of measuring the expression level of miRNA can be performed by, for example, quantitative or semi-quantitative real-time PCR, northern blotting analysis, or liquid hybridization.

In some embodiments, calculating the normalized CT value included two methods. One was normalized by U6 small nuclear RNA (RNU6). This method used the CT value of RNU6 in the miRNA array as a reference, and the expression level of miRNA was transferred by the formula $2^{-\Delta CT}$, wherein the $\Delta CT$ was obtained from "subtracting the CT value of RNU6 from the CT value of the cDNA of the target miRNA." The other was that the average CT value of all detected miRNAs in the miRNA array was being as a reference. The expression level of miRNA was transferred by the formula $2^{-\Delta CT}$, wherein the $\Delta CT$ was obtained from "subtracting the average CT value from the CT value of the cDNA of the target miRNA."

In the present disclosure, the sensitivity and specificity of encapsulating peritoneal sclerosis detection were obtained from the ROC curve. For example, the ROC curve was drawn by the software "Prism" through inputting the normalized data of the expression level of the miRNA, and the default values was used in the calculation portion. Then, the relative value of the maxima likelihood ratio was chosen as a cutoff value, and the sensitivity and specificity were obtained by the cutoff value.

In addition, some examples further included testing different combinations of miRNAs. As for calculating the expression level of each miRNA, the model equation was established by the multivariate logistic regression to estimate the risk of encapsulating peritoneal sclerosis.

In some embodiment, the present disclosure provides a use of miRNA detecting reagent for manufacture of a kit for risk determination of encapsulating peritoneal sclerosis, wherein the miRNA is selected from group consisting of miR-17, miR-100, miR-155, miR-202, miR-422a, miR-483, and combinations thereof.

In some embodiment, the detected sequences of miRNAs are derived from human, wherein miR-17 is hsa-miR-17-5p (SEQ ID NO. 1), miR-100 is hsa-miR-100-5p (SEQ ID NO. 2), miR-155 is hsa-miR-155-5p (SEQ ID NO. 3), miR-202 is hsa-miR-202-3p (SEQ ID NO. 4), miR-422 is hsa-miR-422a (SEQ ID NO. 5), and miR-483 is hsa-miR-483-5p (SEQ ID NO. 6). The miRNAs and its miRBase Mature sequence accession number are hsa-miR-17-5p (MIMAT0000070), hsa-miR-100-5p (MIMAT0000098), hsa-miR-155-5p (MIMAT0000646), hsa-miR-202-3p (MIMAT0002811), hsa-miR-422a (MIMAT0001339), and hsa-miR-483-5p (MIMAT0004761).

In some embodiment, the kit may be in the form of a reagent kit. The kit further includes common reagents for PCR, such as primers or probes for detecting miRNA, buffer, deoxy-ribonucleotide triphosphate (dNTP), magnesium chloride, distilled water, and Taq polymerase.

In some embodiment, the probes or primers may be fixed on the solid support, such as chip.

Encapsulated peritoneal sclerosis (EPS) is a rare and serious complication of long-term peritoneal dialysis (PD), in which the increase in long-term peritoneal dialysis mortality may be positively correlated with the severity of ESP. The diagnosis of EPS requires imaging (eg. abdominal X-ray, abdominal computed tomography, ultrasound examination) and invasive laparoscopy. When the patient is diagnosed with EPS, the treatment method is to terminate the peritoneal dialysis and switch to hemodialysis treatment, drug treatment, or treatment in both aforementioned two ways at the same time. Drugs include immunosuppressants or anti-fibrotic drugs, wherein the immunosuppressants include Corticosteroids, Colchicine, Azathioprine, Cyclosporine, Mycophenolate mofetil (MMF), or mTOR inhibitors, etc., wherein the anti-fibrotic drugs include Tamoxifen.

EPS can also occur in patients who have not undergone peritoneal dialysis, such as liver cirrhosis with accumulation of ascites, post-abdominal surgery, patients with drugs that use β-blockers, autoimmune diseases, abdominal malignant tumors patients, or idiopathic diseases etc.

Example 1

The Prediction of Encapsulating Peritoneal Sclerosis by Single miRNA 1.1 Collecting Specimens Samples were obtained from long-term peritoneal dialysis patients (regular dialysis for more than 3 months), and 80 patients were selected for further analyzing the correlation between microRNAs and encapsulating peritoneal sclerosis. The patients who have been diagnosed with encapsulating peritoneal sclerosis (17 patients in the EPS group) was analyzed the difference in miRNA expression between patients with and without encapsulating peritoneal sclerosis (63 patients in the control group) for evaluating whether the miRNA can be used as a biomarker for screening encapsulating peritoneal sclerosis or not.

1.2 Extraction and Quantification of miRNA

In a conventional method, total miRNA in the patient's ascites was extracted, and 600 ng of the total miRNA was reverse-transcribed following by the protocol of TaqMan® MicroRNA Reverse Transcriptase to obtain cDNAs. The cDNAs were then preceded with miRNA array according to the protocol provided by the TaqMan® Array Human MicroRNA A Cards v2.0. Specifically, the fluorescent probes provided by the TaqMan® were used to detect the cDNAs of: miR-17 (SEQ ID NO.1), miR-100 (SEQ ID NO.2), miR-155 (SEQ ID NO.3), miR-202 (SEQ ID NO.4), miR-422a (SEQ ID NO.5), miR-483 (SEQ ID NO.6), miR-518e (has-miR-518e-3p, MIMAT0002861, SEQ ID NO.7) and miR-597 (has-miR-597-5p, MIMAT0003265, SEQ ID NO.8), and the fluorescent substances were released while an amplification reaction was performed. The fluorescence intensities were detected to obtain the CT values of cDNAs of miR-17, miR-100, miR-155, miR-202, miR-422a, miR-483, miR-518e, and miR-597. Finally, RNU6 was used for normalization, $\Delta CT$ was obtained from subtracting the CT value of RNU6 from the CT value of the cDNA of the miRNA, and the expression level was converted from the logarithmic value of formula $2^{-\Delta CT}$.

FIGS. 2 to 7 were scatter plots that respectively showed six miRNAs in the control and the EPS group, wherein the mark "*", "", and "*" were respectively considered having significant differences of P<0.05, P<0.01, and P<0.001. FIGS. 2 to 7 showed that the expression levels of miR-17, miR-100, miR-155, miR-202, miR-422a, or miR-483 in the EPS group were less than the control group (the patient without encapsulating peritoneal sclerosis). Therefore, at least one of the miRNAs (miR-17, miR-100, miR-155, miR-202, miR-422a, or miR-483) can be used as a biomarker to estimate the risk for the subject suffering from encapsulating peritoneal sclerosis.

Example 2

Prediction of the Encapsulating Peritoneal Sclerosis by the Ratio of Two miRNAs Expression Level The control group and the EPS group were the same as section 1.1 of Example 1, and the miRNAs of the control group and the EPS group were obtained from section 1.2 of Example 1. Table 1 showed the ratios of ten groups of the miRNAs expression levels for estimating the risk for the subject suffering from encapsulating peritoneal sclerosis.

TABLE 1

The ratios of ten groups of the miRNAs expression levels

| Group | Ratios of the miRNAs expression levels |
|---|---|
| 1 | miR-422a/miR-17 = ratio A |
| 2 | miR-202/miR-483 = ratio B |
| 3 | miR-422a/miR-483 = ratio C |
| 4 | miR-202/miR-155 = ratio D |
| 5 | miR-202/miR-17 = ratio E |
| 6 | miR-100/miR-17 = ratio F |
| 7 | miR-155/miR-17 = ratio G |
| 8 | miR-100/miR-483 = ratio H |
| 9 | miR-202/miR-422a = ratio I |
| 10 | miR-155/miR-483 = ratio J |

FIGS. 8 to 17 were scatter plots that respectively showed ten miRNAs in the control and the EPS group, wherein the mark "*", "", and "*" were respectively considered having significant differences of P<0.05, P<0.01, and P<0.001. FIGS. 8 to 17 showed that the ratios of ten groups of the miRNAs expression levels in the EPS group were less than that of the control group (the patient without encapsulating peritoneal sclerosis). Therefore, at least one of the ratios of the miRNAs expression levels can be used as a biomarker for estimating the risk for the subject suffering from encapsulating peritoneal sclerosis.

Example 3

Prediction of the Encapsulating Peritoneal Sclerosis by Cutoff Value of the Ratio of Two miRNAs Expression Level The ratios of ten groups (ratio A to ratio J) in the control group and the EPS group were chosen from Example 2, and were respectively predicted by Logistic regression analysis. The predictive probability of encapsulating peritoneal sclerosis with the best sensitivity and specificity was selected as a cutoff value, and ten receiver operating characteristic curves were plotted. The area under curve (AUC) of ROC curve was calculated, and there's no discrimination when the AUC=0.5. The more the AUC value, the stronger the discrimination. Table 2 below showed that the area under curve of the ratios of these miRNAs expression levels were at least greater than 0.6.

TABLE 2

Analysis of receiver operating characteristics

| Group | Ratios of the miRNAs expression levels | AUC | Cutoff value |
|---|---|---|---|
| 1 | miR-422a/miR-17 = ratio A | 0.779 | 0.2127 |
| 2 | miR-202/miR-483 = ratio B | 0.772 | 0.2017 |
| 3 | miR-422a/miR-483 = ratio C | 0.769 | 0.1938 |
| 4 | miR-202/miR-155 = ratio D | 0.754 | 5.281 |
| 5 | miR-202/miR-17 = ratio E | 0.747 | 0.09099 |
| 6 | miR-100/miR-17 = ratio F | 0.739 | 2.718 |
| 7 | miR-155/miR-17 = ratio G | 0.716 | 0.28 |
| 8 | miR-100/miR-483 = ratio H | 0.701 | 2.448 |
| 9 | miR-202/miR-422a = ratio I | 0.699 | 1.045 |
| 10 | miR-155/miR-483 = ratio J | 0.687 | 0.08035 |

Table 2 showed the ratios of the miRNAs expression levels, and the ratio A to ratio J in the EPS groups were less than its cutoff values. Such as, the ratio A of the EPS group was less than its cutoff value, the ratio B of the EPS group was less than its cutoff value, and so forth. Therefore, at least one of the ratios of the two miRNAs expression levels is less than its cutoff value, and the subject is estimated having high risk of suffering from encapsulating peritoneal sclerosis.

Comparative Example 1

The control group and the EPS group were the same as section 1.1 of Example 1, and the miRNAs of the control group and the EPS group were obtained from section 1.2 of Example 1. Table 3 showed the ratios of ten groups of the miRNAs expression levels different from Table 1 for analyzing whether the ratios can be used for estimating the risk for the subject suffering from encapsulating peritoneal sclerosis or not. The analysis method was the same as Example 3, and the area under curve of ROC curve was calculated.

TABLE 3

Analysis of receiver operating characteristics

| Ratios of the miRNAs expression levels | AUC |
|---|---|
| miR-483-5p/miR-17 | 0.528 |
| miR-483-5p/miR-597 | 0.525 |
| miR-483-5p/miR-100 | 0.52 |
| miR-597/miR-202 | 0.514 |
| miR-597/miR-483-5p | 0.507 |
| miR-17/miR-483-5p | 0.506 |
| miR-155/miR-597 | 0.504 |
| miR-422a/miR-597 | 0.503 |
| miR-100/miR-597 | 0.502 |
| miR-597/miR-155 | 0.501 |

As shown in Table 3, although at least one of the miRNAs in each group was the same as in Example 3, the AUC values in different combinations of the miRNAs closed to 0.5 were considered no discrimination.

Example 4

Prediction of the Encapsulating Peritoneal Sclerosis by Cutoff Values of the Ratio of Five miRNAs Expression Level at the Same Time The ratios of five groups in the control group and the EPS group from Example 3 (ratio A to ratio E) were used for the model equation prediction by Logistic regression analysis.

$$\text{Prediction score } S = -4.088 + (1.957*V) + (2.271*W) + (1.109*X) + (1.904*Y) - (0.108*Z) \quad \text{equation (11)}.$$

When the ratio A was less than or equal to 0.2127, V=1, when the ratio A was more than 0.2127, V=0; when the ratio B was less than or equal to 0.2017, W=1, when the ratio B was more than 0.2017, W=0; when the ratio C was less than or equal to 0.1938, X=1, when the ratio C was more than 0.1938, X=0; when the ratio D was less than or equal to 5.281, Y=1, when the ratio D was more than 5.281, Y=0; and when the ratio E was less than or equal to 0.09099, Z=1, when the ratio E was more than 0.09099, Z=0. The ratios were analyzed by ROC curve, and the results were shown in Table 4 and FIG. 18.

TABLE 4

The relation among cutoff value, sensitivity and specificity in ROC curve

| Cutoff value | sensitivity | specificity |
|---|---|---|
| >−3.534 | 1.0000 | 0.4118 |
| >−2.609 | 1.0000 | 0.4265 |
| >−2.212 | 1.0000 | 0.4412 |
| >−2.158 | 0.9756 | 0.4706 |
| >−2.028 | 0.9756 | 0.5441 |
| >−1.871 | 0.9512 | 0.5441 |
| >−1.474 | 0.9024 | 0.6471 |
| >−1.076 | 0.9024 | 0.6765 |

TABLE 4-continued

The relation among cutoff value, sensitivity
and specificity in ROC curve

| Cutoff value | sensitivity | specificity |
|---|---|---|
| >−0.9190 | 0.8780 | 0.7206 |
| >−0.7620 | 0.8780 | 0.7353 |
| >−0.5215 | 0.8049 | 0.8235 |
| >−0.2810 | 0.7805 | 0.8235 |
| >−0.1240 | 0.7561 | 0.8382 |
| >0.005500 | 0.7073 | 0.9118 |
| >0.0595 | 0.6829 | 0.9265 |
| >0.4845 | 0.6585 | 0.9559 |
| >0.9850 | 0.6341 | 0.9559 |
| >1.115 | 0.5854 | 0.9559 |
| >1.195 | 0.4390 | 0.9706 |
| >1.593 | 0.3902 | 0.9853 |
| >2.491 | 0.3659 | 0.9853 |

Figure 18:
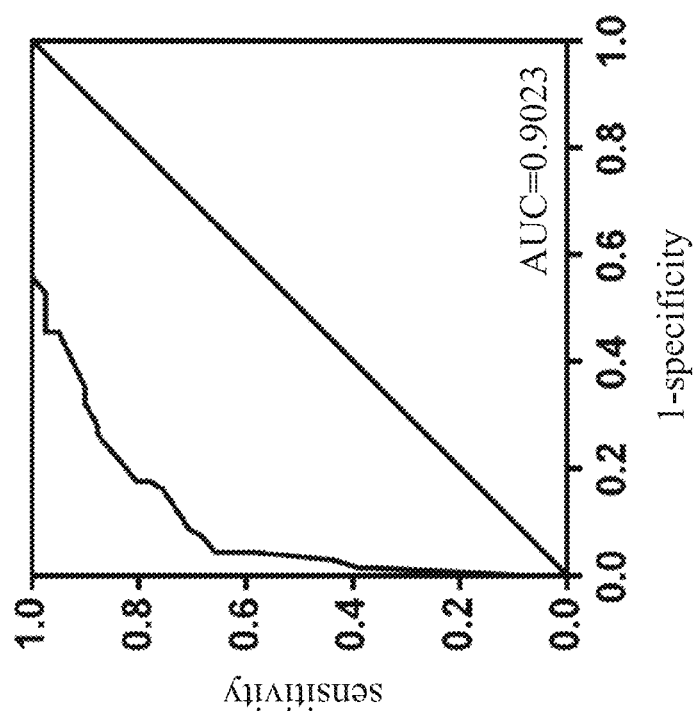
FIG. 18 shows the result of five miRNAs expression levels analyzing by the receiver operating characteristic (ROC) curve at the same time.

As shown in FIG. 18, the area under curve was 0.9023 indicating a high discriminating ability. As shown in Table 4 above, when the cutoff value is −0.5215, the sensitivity is 80.49% and the specificity is 82.35%. Therefore, simultaneous use of four miRNAs to predict encapsulating peritoneal sclerosis can obtain accurate prediction results.

Example 5

Figure 19:
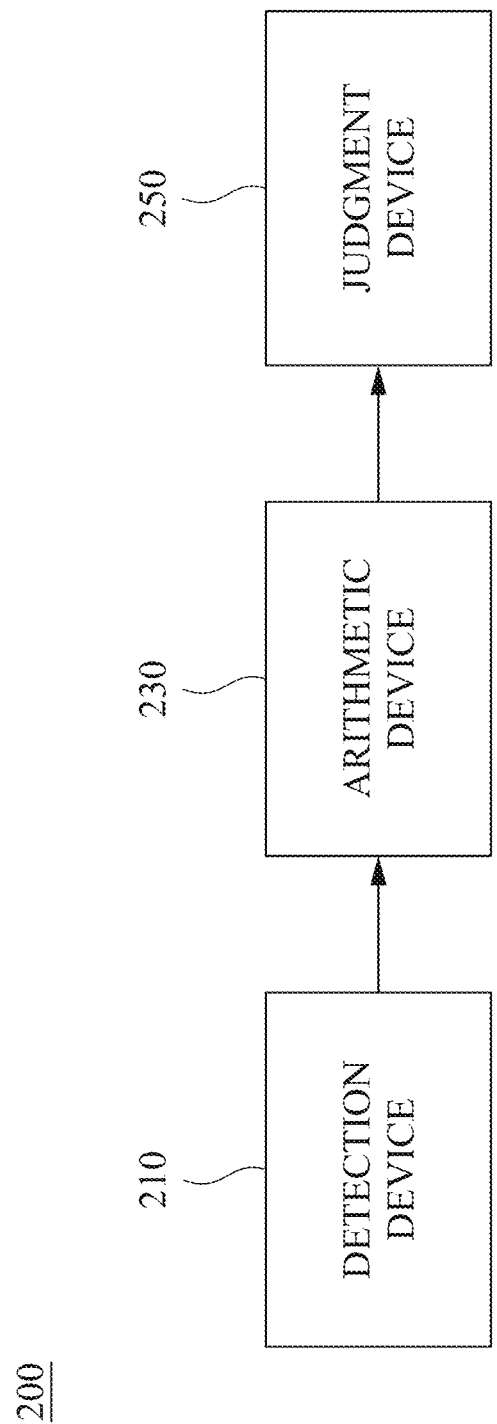
FIG. 19 is an exemplary drawing illustrating an analyzer for estimating a risk for a subject suffering from an encapsulating peritoneal sclerosis in according to one embodiment of the present disclosure.

As shown in FIG. 19, which is an exemplary drawing illustrating an analyzer for estimating a risk for a subject suffering from an encapsulating peritoneal sclerosis in according to one embodiment of the present disclosure. The analyzer 200 includes a detection device 210, an arithmetic device 230, and a judgment device 250.

The detection device 210 detects in a specimen miRNAs comprises miR-17, miR-100, miR-155, miR-202, miR-422a, miR-483, or a combination thereof, wherein the calculation method of the expression level as described in above example 1 section 1.2.

The arithmetic device 230 perform arithmetic operations on the expression levels of the miRNAs, the arithmetic operations include:

(1) as in example 1, comparing the expression level of at least one or a plurality of miRNAs: miR-17, miR-100, miR-155, miR-202, miR-422a, or miR-483 in the sample to that of a same miRNA(s) of a control to obtain a comparing result;

(2) as in example 2, calculating a first ratio obtained from dividing one of the expression levels of the two miRNAs by the other one of the expression levels of the two miRNAs of the sample of the subject (as shown in Table 1); calculating a second ratio obtained from dividing one of the expression levels of the two miRNAs by the other one of the expression levels of the two miRNAs of the control (as shown in Table 1); and comparing the first ratio and the second ratio to obtain a comparing result;

(3) as in example 3, calculating a first ratio obtained from dividing one of the expression levels of the two miRNAs by the other one of the expression levels of the two miRNAs of the sample of the subject (as shown in Table 2); predicting by Logistic regression analysis and selecting the predictive probability of encapsulating peritoneal sclerosis with the best sensitivity and specificity as a cutoff value; and comparing the first ratio and the cutoff value to obtain a comparing result; or (4) as in example 4, calculating a plurality of first ratios obtained from dividing one of the expression levels of the two miRNAs by the other one of the expression levels of the two miRNAs of the sample of the subject (as shown in Table 2, ratio A to ratio E); performing arithmetic operations on the ratios A to E to obtain a prediction score $S=-4.088+(1.957*V)+(2.271*W)+(1.109*X)+(1.904*Y)-(0.108*Z)$, wherein when the first ratio A is less than or equal to 0.2127, $V=1$, when the first ratio A is more than 0.2127, $V=0$; when the first ratio B is less than or equal to 0.2017, $W=1$, when the first ratio B is more than 0.2017, $W=0$; when the first ratio C is less than or equal to 0.1938, $X=1$, when the first ratio C is more than 0.1938, $X=0$; when the first ratio D is less than or equal to 5.281, $Y=1$, when the first ratio D is more than 5.281, $Y=0$; and when the first ratio E is less than or equal to 0.09099, $Z=1$, when the first ratio E is more than 0.09099, $Z=0$, providing a reference value S0; and estimating the risk for the subject suffering from the encapsulating peritoneal sclerosis to obtain a comparing result.

The judgment device 250 determines the comparing result, wherein the comparing result is used for estimating the risk for a subject suffering from the encapsulating peritoneal sclerosis, comprising:

(1) as in example 1, when the expression level of miRNA in the control is higher than that of the sample, the subject is estimated having a risk of suffering from the encapsulating peritoneal sclerosis, vice versa;

(2) as in example 2, when the first ratio is higher than the second ratio, the subject is estimated having a risk of suffering from the encapsulating peritoneal sclerosis, vice versa;

(3) as in example 3, when the first ratio is lower than the cutoff value, the subject is estimated having a risk of suffering from the encapsulating peritoneal sclerosis, vice versa; or (4) as in example 4, when the prediction score S is lower than the reference value S0, the subject is estimated having a risk of suffering from the encapsulating peritoneal sclerosis, vice versa.

The judgment device 250 further advises the subject with a suitable therapy based on the comparing result. The suitable therapy includes, but is not limited to terminate the peritoneal dialysis and switch to hemodialysis treatment, drug treatment, or treatment in both aforementioned two ways at the same time. Drugs include immunosuppressants or anti-fibrotic drugs, wherein the immunosuppressants include Corticosteroids, Colchicine, Azathioprine, Cyclosporine, Mycophenolate mofetil (MMF), or mTOR inhibitors, etc., wherein the anti-fibrotic drugs include Tamoxifen.

While the disclosure has been described by way of example(s) and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for treating encapsulating peritoneal sclerosis in a human undergoing peritoneal dialysis, the method comprising steps of:
   measuring an expression level of at least two micro ribonucleic acids (miRNAs) in an ascites sample of the human, wherein the at least two miRNAs comprise miR-17 and miR-422a;
   comparing the expression level of the miRNAs in the ascites sample to that of the same miRNAs of a control, wherein when the expression level of the miRNA in the ascites sample is lower than that of the control, the human is estimated as having a risk of suffering from encapsulating peritoneal sclerosis; and
   administering a treatment for encapsulating peritoneal sclerosis to the human who is estimated as having the risk of suffering from encapsulating peritoneal sclerosis with a suitable therapy, wherein the treatment comprises hemodialysis treatment, drug treatment, or a combination thereof.

2. The method of claim 1, wherein the control is obtained from a group of humans without encapsulating peritoneal sclerosis.

3. A method for treating encapsulating peritoneal sclerosis in a human undergoing peritoneal dialysis, the method comprising steps of:
   measuring expression levels of two miRNAs in an ascites sample of the human, wherein the two miRNAs comprise miR-422a and miR-17;
   calculating a first ratio, the first ratio obtained from dividing one of the expression levels of the two miRNAs by the other one of the expression levels of the two miRNAs of the ascites sample of the human; wherein the first ratio in the step of calculating is obtained from calculating the expression levels of the two miRNAs in the sample of the human by formulae (1):

$$\frac{\text{expression level of miR-422a}}{\text{expression level of miR-17}} = \text{a first ratio A}; \quad \text{formula (1)}$$

providing a reference value comprising calculating the reference value, wherein the reference value is a second ratio obtained by dividing the expression level of one of the two miRNAs in a control sample by the expression level of the other one of the two miRNAs in the control sample, wherein the two miRNAs of the control are the same as that of the human, wherein the second ratio is obtained from calculating the expression levels of the two miRNAs in the sample of the control by formulae (1-1):

$$\frac{\text{expression level of miR-422a}}{\text{expression level of miR-17}} = \text{a second ratio A}; \quad \text{formula (1-1)}$$

comparing the first ratio and the reference value to obtain a comparing result, wherein the comparing result is that the first ratio A is less than the second ratio A, the human is estimated as having the risk of suffering from encapsulating peritoneal sclerosis, and
   administering a treatment for encapsulating peritoneal sclerosis to the human who is estimated as having the risk of suffering from encapsulating peritoneal sclerosis with a suitable therapy, wherein the treatment comprises hemodialysis treatment, drug treatment, or a combination thereof.

4. The method of claim 3, wherein the control is obtained from a group of humans without encapsulating peritoneal sclerosis.

5. A method for treating encapsulating peritoneal sclerosis in a human undergoing peritoneal dialysis, the method comprising steps of:
   measuring expression levels of two miRNAs in an ascites sample of the human, wherein the two miRNAs comprise miR-422a and miR-17;
   calculating a first ratio, the first ratio obtained from dividing one of the expression levels of the two miRNAs by the other one of the expression levels of the two miRNAs of the sample of the human; wherein the first ratio in the step of calculating is obtained from calculating the expression levels of the two miRNAs in the sample of the human by formulae (1):

$$\frac{\text{expression level of miR-422a}}{\text{expression level of miR-17}} = \text{a first ratio A}; \quad \text{formula (1)}$$

providing a reference value;
   comparing the first ratio and the reference value to obtain a comparing result, wherein the step of comparing the first ratio and the reference value comprises when the comparing result is that: when the first ratio A is less than or equal to a reference A0, the human is estimated as having the risk of suffering from encapsulating peritoneal sclerosis, wherein the reference A0 is 0.2127; and
   administering a treatment for encapsulating peritoneal sclerosis to the human who is estimated as having the risk of suffering from encapsulating peritoneal sclerosis with a suitable therapy, wherein the treatment comprises hemodialysis treatment, drug treatment, or a combination thereof.

6. A method for treating encapsulating peritoneal sclerosis in a human undergoing peritoneal dialysis, the method comprising steps of:
   measuring expression levels of a miRNA in an ascites sample of the human, wherein the miRNA comprises miR-17, miR-155, miR-202, miR-422a, and miR-483;
   calculating a plurality of first ratios, the first ratios obtained from calculating the expression levels of the plurality of the miRNAs in the ascites sample of the human by the following formulae:

$$\frac{\text{expression level of miR-422a}}{\text{expression level of miR-17}} = \text{a first ratio A}; \quad \text{formula (1)}$$

$$\frac{\text{expression level of miR-202}}{\text{expression level of miR-483}} = \text{a first ratio B}; \quad \text{formula (2)}$$

$$\frac{\text{expression level of miR-422a}}{\text{expression level of miR-483}} = \text{a first ratio C}; \quad \text{formula (3)}$$

$$\frac{\text{expression level of miR-202}}{\text{expression level of miR-155}} = \text{a first ratio D}; \quad \text{formula (4)}$$

and

-continued $$\frac{\text{expression level of miR-202}}{\text{expression level of miR-17}} = \text{a first ratio E;} \quad \text{formula (5)}$$

calculating the first ratios A, B, C, D, and E to obtain a prediction score S;

providing a reference value S0;

estimating the risk for the human suffering from encapsulating peritoneal sclerosis, wherein when the prediction score S is less than or equal to the reference value S0, the human is estimated as having the risk of suffering from encapsulating peritoneal sclerosis, and administering a treatment for encapsulating peritoneal sclerosis to the human who is estimated as having the risk of suffering from encapsulating peritoneal sclerosis with a suitable therapy, wherein the treatment comprises hemodialysis treatment, drug treatment, or a combination thereof.

7. The method of claim 6, wherein the prediction score S is obtained from calculating the expression levels of the plurality of the miRNAs with an equation below:

prediction score $S=-4.088+(1.957*V)+(2.271*W)+(1.109*X)+(1.904*Y)-(0.108*Z)$     equation (11), wherein when the first ratio A is less than or equal to 0.2127, V=1, when the first ratio A is more than 0.2127, V=0; when the first ratio B is less than or equal to 0.2017, W=1, when the first ratio B is more than 0.2017, W=0; when the first ratio C is less than or equal to 0.1938, X=1, when the first ratio C is more than 0.1938, X=0; when the first ratio D is less than or equal to 5.281, Y=1, when the first ratio D is more than 5.281, Y=0; and when the first ratio E is less than or equal to 0.09099, Z=1, when the first ratio E is more than 0.09099, Z=0.

8. The method of claim 6, wherein the step of providing the reference value S0 comprises:

measuring expression levels of a miRNA in samples of a group of humans with and without encapsulating peritoneal sclerosis, wherein the miRNA comprises one or more of miR-17, miR-155, miR-202, miR-422a, and miR-483; and calculating a plurality of second ratios, the second ratios obtained from calculating the expression levels of the plurality of the miRNAs in the samples of the group of the humans without encapsulating peritoneal sclerosis by the following formulae:

$$\frac{\text{expression level of miR-422a}}{\text{expression level of miR-17}} = \text{a second ratio A;} \quad \text{formula (1-1)}$$

$$\frac{\text{expression level of miR-202}}{\text{expression level of miR-483}} = \text{a second ratio B;} \quad \text{formula (2-1)}$$

$$\frac{\text{expression level of miR-422a}}{\text{expression level of miR-483}} = \text{a second ratio C;} \quad \text{formula (3-1)}$$

$$\frac{\text{expression level of miR-202}}{\text{expression level of miR-155}} = \text{a second ratio D;} \quad \text{formula (4-1)}$$

and $$\frac{\text{expression level of miR-202}}{\text{expression level of miR-17}} = \text{a second ratio E;} \quad \text{formula (5-1)}$$

calculating a plurality of third ratios, the third ratios obtained from calculating the expression levels of the plurality of the miRNAs in the samples of the group of the humans with encapsulating peritoneal sclerosis by the following formulae:

$$\frac{\text{expression level of miR-422a}}{\text{expression level of miR-17}} = \text{a third ratio A;} \quad \text{formula (1-2)}$$

$$\frac{\text{expression level of miR-202}}{\text{expression level of miR-483}} = \text{a third ratio B;} \quad \text{formula (2-2)}$$

$$\frac{\text{expression level of miR-422a}}{\text{expression level of miR-483}} = \text{a third ratio C;} \quad \text{formula (3-2)}$$

$$\frac{\text{expression level of miR-202}}{\text{expression level of miR-155}} = \text{a third ratio D;} \quad \text{formula (4-2)}$$

and $$\frac{\text{expression level of miR-202}}{\text{expression level of miR-17}} = \text{a third ratio E;} \quad \text{formula (5-2)}$$

calculating the second ratios A, B, C, D, and E and the third ratios A, B, C, D, and E by a receiver operating characteristic curve to obtain a cutoff value as the reference value S0.

* * * * *

SEQUENCE LISTING

<160> NUMBER OF SEQ ID NOS: 8

<210> SEQ ID NO 1
<211> LENGTH: 23

-continued

```
<212> TYPE: RNA
<213> ORGANISM: Homo sapiens

<400> SEQUENCE: 1
caaagugcuu acagugcagg uag                                              23

<210> SEQ ID NO 2
<211> LENGTH: 22
<212> TYPE: RNA
<213> ORGANISM: Homo sapiens

<400> SEQUENCE: 2
aacccguaga uccgaacuug ug                                               22

<210> SEQ ID NO 3
<211> LENGTH: 24
<212> TYPE: RNA
<213> ORGANISM: Homo sapiens

<400> SEQUENCE: 3
uuaaugcuaa ucgugauagg gguu                                             24

<210> SEQ ID NO 4
<211> LENGTH: 20
<212> TYPE: RNA
<213> ORGANISM: Homo sapiens

<400> SEQUENCE: 4
agagguauag ggcaugggaa                                                  20

<210> SEQ ID NO 5
<211> LENGTH: 22
<212> TYPE: RNA
<213> ORGANISM: Homo sapiens

<400> SEQUENCE: 5
acuggacuua gggucagaag gc                                               22

<210> SEQ ID NO 6
<211> LENGTH: 22
<212> TYPE: RNA
<213> ORGANISM: Homo sapiens

<400> SEQUENCE: 6
aagacgggag gaaagaaggg ag                                               22

<210> SEQ ID NO 7
<211> LENGTH: 21
<212> TYPE: RNA
<213> ORGANISM: Homo sapiens

<400> SEQUENCE: 7
aaagcgcuuc ccuucagagu g                                                21

<210> SEQ ID NO 8
<211> LENGTH: 22
<212> TYPE: RNA
<213> ORGANISM: Homo sapiens

<400> SEQUENCE: 8
ugugucacuc gaugaccacu gu                                               22
```